US012708549B2

(12) United States Patent
Howard et al.

(10) Patent No.: US 12,708,549 B2
(45) Date of Patent: Aug. 18, 2026

(54) OSTOMY APPLIANCE

(71) Applicant: SALTS HEALTHCARE LIMITED, West Midlands (GB)

(72) Inventors: Lee Howard, West Midlands (GB); Lee Smith, West Midlands (GB)

(73) Assignee: SALTS HEALTHCARE LIMITED, West Midlands (GB)

( * ) Notice: Subject to any disclaimer, the term of this patent is extended or adjusted under 35 U.S.C. 154(b) by 231 days.

(21) Appl. No.: 18/836,559

(22) PCT Filed: Feb. 22, 2023

(86) PCT No.: PCT/GB2023/050391
§ 371 (c)(1),
(2) Date: Aug. 7, 2024

(87) PCT Pub. No.: WO2023/161617
PCT Pub. Date: Aug. 31, 2023

(65) Prior Publication Data

US 2025/0161095 A1 May 22, 2025

(30) Foreign Application Priority Data

Feb. 22, 2022 (GB) ..................................... 2202401

(51) Int. Cl.
*A61F 5/44* (2006.01)
*A61F 5/445* (2006.01)

(52) U.S. Cl.
CPC ............ *A61F 5/4407* (2013.01); *A61F 5/445* (2013.01)

(58) Field of Classification Search
CPC ........ A61F 5/44; A61F 5/4404; A61F 5/4405; A61F 5/4407; A61F 5/4408; A61F 5/442; A61F 5/445; A61F 2005/4415
See application file for complete search history.

(56) References Cited

U.S. PATENT DOCUMENTS 6,045,542 A 4/2000 Cawood
8,562,578 B2 * 10/2013 Richmann ............ A61F 5/4405 604/335

(Continued)

FOREIGN PATENT DOCUMENTS

EP 1214028 B1 7/2004
WO 2001021115 A1 3/2004

(Continued)

OTHER PUBLICATIONS

Examination Report issued by the United Kingdom Intellectual Property Office for Application No. GB2202401.2 dated Jul. 10, 2025 (5 pages).

(Continued)

*Primary Examiner* — Philip R Wiest
(74) *Attorney, Agent, or Firm* — Michael Best & Friedrich LLP

(57) ABSTRACT

An ostomy appliance including an internal collecting volume defined by a first wall and a second wall connected together about a periphery, a stoma receiving opening defined in the first wall, a comfort layer positioned adjacent the second wall and attached about the periphery, an outlet portion which includes a valve having an outlet, the valve having a closed condition, in which waste is prevented or inhibited from exiting through the outlet, and an open condition, in which waste is permitted to exit through the outlet, and a support panel which extends across the first or second wall and provides an opening, wherein the outlet portion has a stowed position in which the valve is housed in the opening.

20 Claims, 3 Drawing Sheets

(56) References Cited

U.S. PATENT DOCUMENTS

| | | | | |
|---|---|---|---|---|
| 2005/0273065 | A1* | 12/2005 | Lillegaard | A61F 5/4405 604/332 |
| 2020/0229962 | A1* | 7/2020 | Torstensen | A61F 5/4407 |
| 2023/0025119 | A1* | 1/2023 | Allen | A61F 5/445 |

FOREIGN PATENT DOCUMENTS

| | | | |
|---|---|---|---|
| WO | 2010019313 | A1 | 2/2010 |
| WO | 2013038132 | A1 | 3/2013 |
| WO | 2017066701 | A1 | 4/2017 |
| WO | 2003086249 | A2 | 10/2023 |

OTHER PUBLICATIONS

International Search Report and Written Opinion dated Apr. 20, 2023 for corresponding International Application No. PCT/GB2023/050391 (11 pages).

GB Search Report dated Jun. 14, 2022 for corresponding GB Application No. GB2202401.2 (2 pages).

* cited by examiner

OSTOMY APPLIANCE

CROSS-REFERENCE TO RELATED APPLICATIONS

This application is a national phase filing under 35 § U.S.C. 371 of International Application No. PCT/GB2023/050391, filed on Feb. 22, 2023, which claims priority to British Patent Application No. 2202401.2, filed on Feb. 22, 2022, the entire contents of each of which are incorporated herein by reference.

FIELD OF THE INVENTION

Embodiments of the invention relate to an ostomy appliance.

BACKGROUND OF THE INVENTION

Ostomy appliances are well known in the field. They are typically attached to a user via an adhesive member that extends around the user's stoma with adhesive and provide a collecting volume to collect waste exiting the stoma. A mechanism for draining the collecting volume is often provided—typically, these are in the form of a tap, so that a user can empty waste that is collected in the collecting volume without having to remove and dispose of the entire appliance.

SUMMARY

According to an aspect of the invention we provide an ostomy appliance including:

- an internal collecting volume defined by a first wall and a second wall connected together about a periphery;
- a stoma receiving opening defined in the first wall,
- a comfort layer positioned adjacent the second wall,
- an outlet portion which includes a valve having an outlet, said valve having a closed condition, in which waste is prevented or inhibited from exiting through the outlet, and an open condition, in which waste is permitted to exit through the outlet,
- a support panel which extends across the first or second wall and provides an opening, wherein
- the outlet portion has a stowed position in which the valve is housed in the opening.

The comfort layer may be attached about the periphery. The support panel may extend across the second wall. The comfort layer extends over the support panel.

The support panel may be attached at a position spaced from the periphery. The support panel may be attached across an area extending from the periphery (or adjacent to the periphery but spaced from it) to adjacent the opening. The support panel may be attached on both sides of the opening (i.e. on the same wall of the appliance and to the left and right of an axis extending through the opening)—the attachment may define the transverse extent of the opening. The support panel may be attached along a top portion above the opening and forms a housing extending upwards from the opening.

The support panel may extend around four surfaces of the outlet portion when it is in its stowed position (this may be formed from the panel extending around and over the outlet portion and a proximal wall, which may be the second wall defining the internal collecting volume).

The support panel may include or may be attached to an extension portion. The extension portion may extend towards a bottom portion of the comfort layer. The comfort layer may be connected to the support panel or may be connected to the extension portion.

The outlet portion may include an engagement formation. The engagement formation may be for engaging a corresponding formation to hold the outlet portion in the stowed position. The engagement formation may be formed or provided on a first wall side of the outlet portion. The corresponding formation may be formed or provided on the support panel. Alternatively, the corresponding formation may be formed or provided on the extension portion. The engagement formation and the corresponding formation may include respective hook-and-loop fasteners.

The support panel may be more rigid than the first and/or second wall (it may be made form a different material and/or may be formed from a thicker layer).

A lower portion of the comfort layer may not be connected to the second wall. A second comfort layer may be provided, which is adjacent the first wall and connected about the periphery.

The valve may include a closure arrangement. The closure arrangement may be moveable between a position blocking the outlet, and a second position in which the outlet is open. The closure arrangement may have a blocking member which is inserted into the outlet when the valve is in its closed condition. The ostomy appliance may be a urostomy appliance/pouch/bag or an ileostomy appliance/bag/pouch.

BRIEF DESCRIPTION OF THE FIGURES

In order that the present disclosure may be more readily understood, preferable embodiments thereof will now be described, by way of example only, with reference to the accompanying drawings, in which.

DETAILED DESCRIPTION

Figures 1, 2:
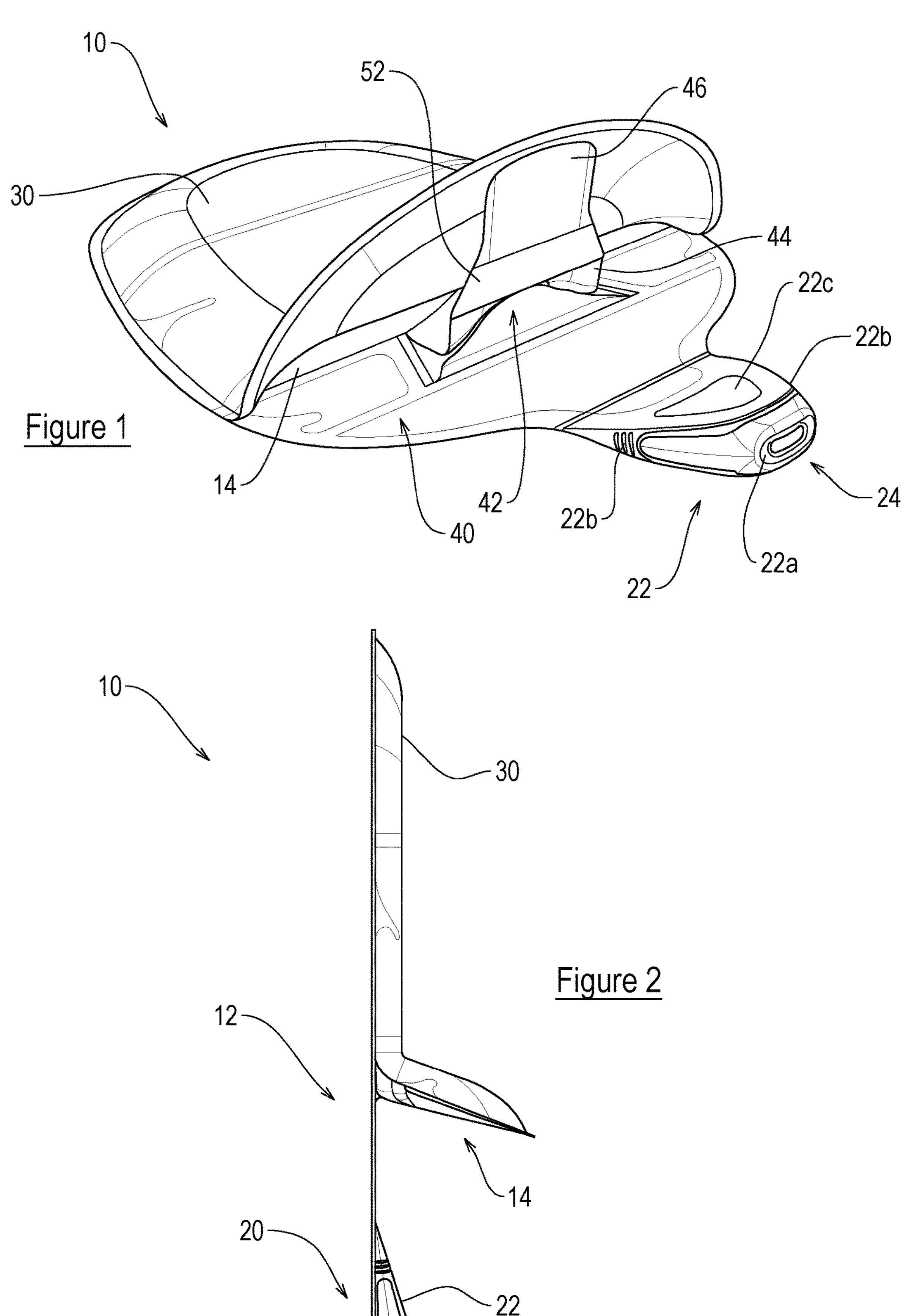
FIG. 1 is a perspective view of an ostomy appliance.
FIG. 2 is a side view of an ostomy appliance.

Referring to the figures, an ostomy appliance 10 (or appliance 10—also known as an ostomy pouch or bag) is illustrated. The ostomy appliance 10 includes a first wall 12, a second wall 14 and a comfort layer 30. The first and second wall 12, 14 are connected together about a periphery to define an internal collecting volume. In the illustrated example, the first wall 12 is on a "body" side of the appliance 10 (i.e. it is closer to the body than the internal collecting volume when the appliance 10 is in use) and the second wall 14 is on a "non-body" side of the appliance 10 (i.e. it is further/furthest from the body than the internal collecting volume when the appliance 10 is in use).

A stoma receiving opening 16 is defined in the first wall 12. The stoma receiving opening 16 is in fluid communication with the internal collecting volume such that in use, waste entering the appliance via the stoma receiving opening flows into the collecting volume. In some embodiments, an adhesive member 18 (shown in FIG. 5) is attached to the first wall 12 and extends around the stoma receiving opening 16. The adhesive member 18 permits a user of the appliance 10 to attach the appliance 10 to their abdomen around their stoma.

The comfort layer 30 is positioned adjacent the second wall 14 and also attached about the periphery. In other words, the comfort layer 30 is attached around the same seam/location as the first and second walls 12, 14 are connected. The comfort layer 30 is also on the "non-body" side of the appliance 10.

In some embodiments, a lower portion of the comfort layer 30 is not connected to the second wall 14. In other words, the comfort layer 30 extends and is attached to the second wall 14 around the majority of the periphery. However, at a bottom part (where the outlet portion 20 is located) the comfort layer 30 is left unattached/provides an opening to access the second wall 14.

In some embodiments, the comfort layer 30 is provided by two sheets of material that provide the front face of the appliance 10. An upper sheet 30*a* is connected to the periphery in an arc over the top of the appliance 10 and a lower sheet 30*b* is connected to the periphery on each side of the appliance 10. The upper sheet 30*a* and the lower sheet 30*b* overlap—the overlap is generally horizontal and aligned with stoma receiving opening 16, so that a user may move the sheets 30*a*, 30*b* apart to observe the interior of the appliance 10, if desired.

Figure 5:
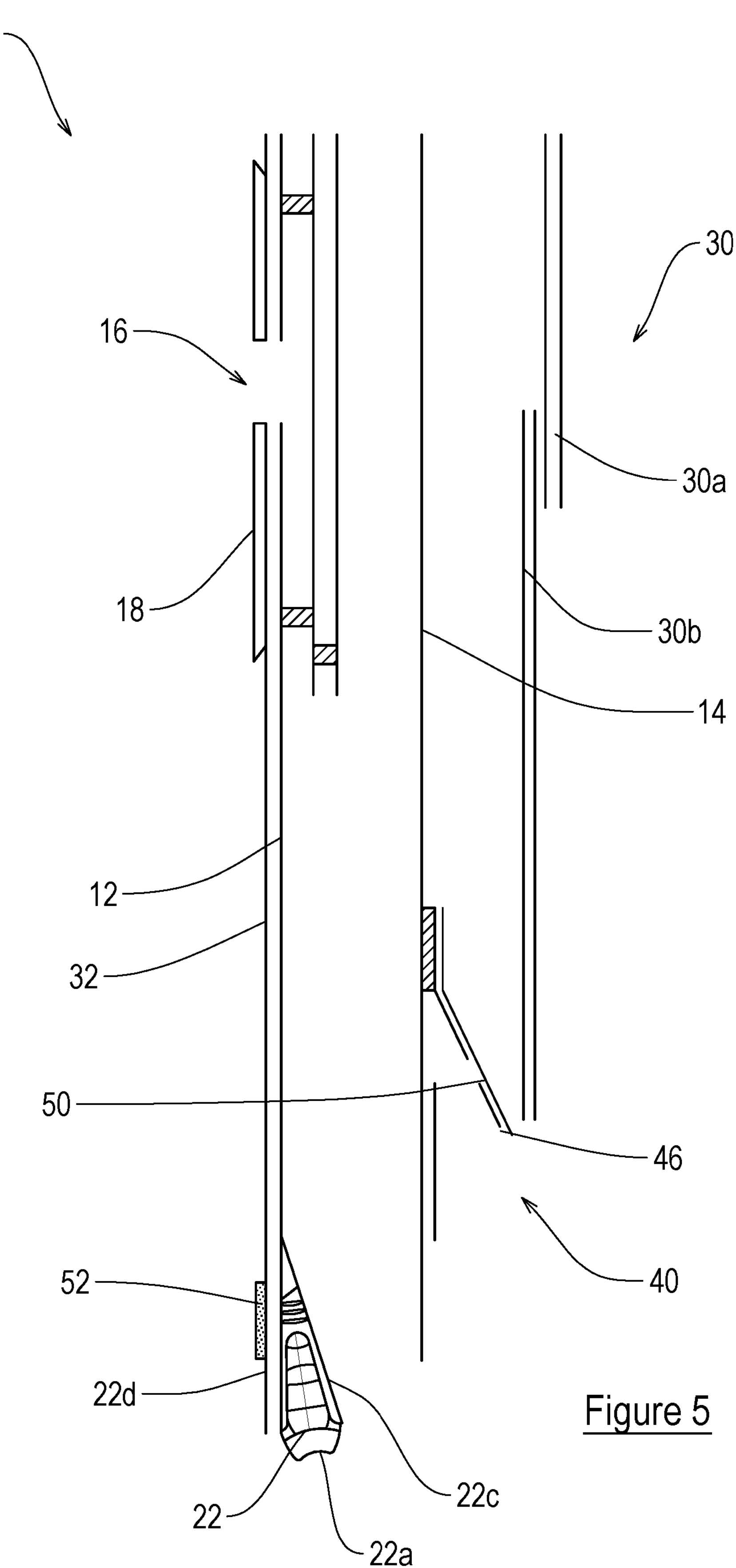
FIG. 5 shows an exploded cross-sectional side view of the arrangement of layers in an ostomy appliance.

In some embodiments, the appliance 10 further includes a second comfort layer 32 adjacent the first wall 12 (see FIG. 5). The second comfort layer 32 is connected about the periphery (in this example, about the entire periphery) and lies against the body in use.

The appliance 10 also includes a support panel 40 and an outlet portion 20. In the illustrated embodiment, the support panel 40 extends across the second wall 14 (but it should be appreciated that the support panel 40 could, in some embodiments, extend across the first wall 12). The support panel 40 provides an opening 42.

It should be appreciated, that the comfort layer could cover one side of the appliance 10 or both sides of the appliance 10. The comfort layer may be attached to the periphery of the appliance 10 or it may form a complete a complete cover into which the appliance 10 is placed. It covers the support panel 40 to improve the usability and appearance of the appliance 10.

In some embodiments, the support panel 40 is attached at a position spaced from the periphery (in the illustrated example, the support panel 40 is attached to the second wall 14 but it should be appreciated that it could be attached to the first wall 12 if it extends across the first wall 12). In other words, the support panel 40 is attached to the second wall 14 between the outside edge of the walls 12, 14/comfort layer 30 and the opening 42.

In some embodiments, the support panel 40 is attached on both sides of the opening 42. In other words, the appliance 10 has a central longitudinal axis and the support panel 40 is attached to the second wall 14 on both sides of the axis (with the opening 42 provided in between and, in this example, generally centrally with respect to the axis).

In some embodiments, the support panel 40 is also attached along a top portion (i.e. above the opening 42). This allows the support panel 40 to form a housing 44 extending upwards from the opening. In other words, the housing 44 is attached to the second wall 14 on three sides with the opening 42 providing an open fourth side (which receives the outlet portion 20).

In some embodiments, the support panel 40 is welded to the second wall 14. The weld extends around the opening 42 and/or around the periphery and/or around the outlet portion 20.

In some embodiments, the support panel 40 is attached across an area of the second wall 14 (rather than just a thin weld line or thin area of adhesive). The area may extend from the periphery to adjacent the opening 42 on one or both sides of the opening 42. A second area may extend from below the opening 42 towards the outlet portion 20. A third area may extend over a face of the outlet portion 20.

In the present examples, the support panel 40 is attached only to the second wall 14 (for example, using a weld or an adhesive or the like) and there is no connection that extends through to the first wall 12 (i.e. none of the walls 12, 14 are attached together in attaching the support panel 40 to the second wall 14, for example). In other words, the support panel 40 only interacts with/is attached to one wall (the second wall 14 or the first wall 12).

In some embodiments, the support panel 40 extends across an entire bottom portion of the second wall 14 and over a face of the valve 22/outlet portion 20 (as discussed above in relation to the areas that may be adhered to the wall 14). In some embodiments, the support panel 40 is more rigid than the first and/or second walls 12, 14 (and the comfort layer 30). In other words, the support panel 40 is flexible but has more structure (is made of a less flexible/more structured material) than the film walls (i.e. flexible and very thin material that forms the walls 12, 14 of the appliance 10). This may be provided simply by using a thicker material than the film of the first and second walls 12, 14.

In some embodiments, the support panel 40 includes or is attached to an extension portion 46. In the illustrated example, the extension portion 46 extends downwards/towards a bottom portion of the comfort layer/towards the end 22*a* of the valve 22 (when the outlet portion 20 is in its unstowed/in use position).

In some embodiments, the support panel 40 connects to the comfort layer 30 (i.e. an exterior surface of the support panel 40 attaches to an interior surface of the comfort layer 30). Alternatively, the extension portion 46 connects to the comfort layer 30 (again, this attachment is between an exterior surface of the extension portion 46 to the interior of the comfort layer 30). The connection may be permanent (e.g. a weld, adhesive or likewise mechanism of attaching the materials together) or removable (e.g. hook-and-loop, gecko tape or the like).

The outlet portion 20 includes a valve 22 having an outlet. The valve 22 has a closed condition and an open condition. In the closed condition, waste is prevented (or at least inhibited) from exiting through the outlet. In the open condition, waste is permitted to exit through the outlet.

Figures 3, 4:
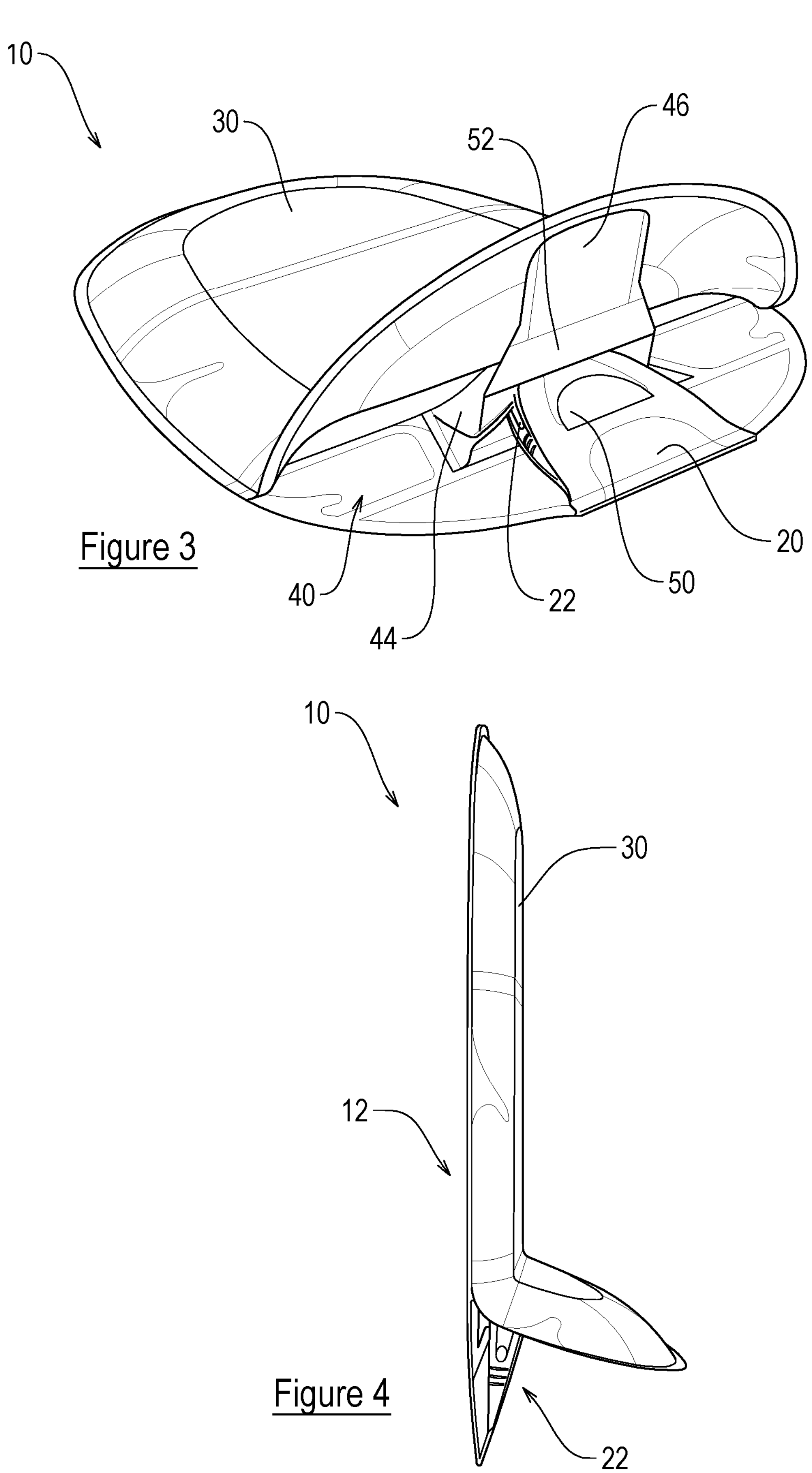
FIG. 3 is a perspective view of an ostomy appliance.
FIG. 4 is a side view of an ostomy appliance.

The outlet portion 20 has a stowed position (see FIGS. 3 and 4) in which the valve 22 is housed in the opening 42. In the shown example, the outlet portion 20 moves to its stowed position by folding upwards/towards the stoma receiving opening. In some embodiments, a fold, crease or cut-out may be provided in a surface material. Thus, the fold line/cut-out/score line, for encouraging the outlet portion 20 to fold to the stowed position in the ideal location, may be provided across a portion of the support panel 40.

In the stowed position, an end of the valve 22 is located within the opening 42 provided by the support panel 40. To reach this position the valve 22 is folded forward/away from the body. This allows the support panel 40 to hold the outlet portion 20 (and valve 22) in position/against the second wall 14 as the internal collecting volume fills with waste during use.

As discussed above, the support panel 40 provides the housing 44. The valve 22 has an end 22*a*, first and second sides 22*b*, a front face 22*c* and a back face 22*d*. Thus, when the outlet portion 20 is in its stowed position in the housing 44, the housing 44 extends around four surfaces of the valve 22 (i.e. the end 22*a*, first and second sides 22*b* and the back face 22*d*). The front face 22*c* lies alongside the second wall 14. In other words, the support panel 40 is connected to the wall 12, 14 and provides a pocket in which the outlet valve may be stowed. When the appliance 10 is being emptied the valve 22 is removed from the pocket and opened to allow waste to flow out of the appliance 10. Then, once used, the valve 22 is stowed away again in the pocket.

It should be appreciated that where the support panel is attached to the first wall, the outlet portion 20 folds back—towards the body—to be stowed as discussed above. In this case, the housing would extend around the end 22*a*, first and second sides 22*b* and the front face 22*c* and the back face 22*d* will lie alongside the first wall 12 or second comfort layer 32.

In some embodiments, the outlet portion 20 includes an engagement formation 50 for engaging a corresponding formation 52 to hold the outlet portion 20 in the stowed position. In the illustrated example, the engagement formation 50 is formed on the first wall side of the outlet portion 20. The corresponding formation 52 is provided on the extension portion 46. In other words, the engagement formation 50 is provided on the back face 22*d* of the valve 20. The corresponding formation 52 is provided on an interior surface of the extension portion 46. Thus, when the outlet portion 20 is folded to its stowed position, the two formations 50, 52 are easily brought into contact to provide an additional mechanism to hold the outlet portion 20 in position.

It should be appreciated that the corresponding formation 52 could be on the support panel 40 (and potentially inside the housing 44) instead of on the extension portion 46. Further, the engagement formation could be provided on the front face 22*d* of the valve 22, with the corresponding formation on the second wall 14 (or support panel 40).

In the present embodiment, the engagement formation 50 and the corresponding formation 52 include respective hook-and-loop fasteners (but this need not be the case, a different removable connection mechanism could be used to hold the outlet portion 20 in the stowed position).

In some embodiments, the valve 22 includes a closure arrangement 24 which is moveable between a position blocking the outlet, and a second position in which the outlet is open. This may entail the closure arrangement 24 having a blocking member, which is inserted into the outlet when the valve 22 is in its closed condition (the blocking member is removed from the outlet when the valve 22 is in its open condition).

Embodiments of the present invention are advantageous because the outlet portion 20 (and, thus, the valve 22) is held by the support panel 40. Particularly when the appliance 10 is in use, the outlet portion 20 is held against the second wall 14 and provides a smooth outline for a user (does not produce a bulge or reduces bulging under clothes, for example). Particularly, since the comfort layer 30 covers the outlet portion 20 and the second wall 14 and hides the outlet portion 20 from sight and smooths the profile.

Importantly, the appliance 10 is particularly suitable for a urostomy or ileostomy. In urostomy, the waste excreted by the stoma is predominantly liquid (e.g. urine or a urine/mucus mix) and has a relatively low viscosity (compared to more solid waste from a colostomy, for example), which means the waste "flows" similarly to water or a runny substance. Thus, the valve 22 must be able to close sufficiently well to prevent liquid leakage. Other ostomy appliances with only an opening in the outlet portion that relies on multiple folds/rolling of the outlet to close are not suitable for a urostomy/ileostomy (i.e. liquid waste) because outlet is not sealed/closed sufficiently well to stop leakage.

However, urostomy valves must be bulkier than their soft closure counterparts (in order to provide liquid sealing) which means they are more difficult to obscure under clothing, for example. The present invention seeks to improve the silhouette of such appliances 10 and thus, improve the user experience for those that have to use such an appliance 10.

When used in this specification and claims, the terms "comprises" and "comprising" and variations thereof mean that the specified features, steps or integers are included. The terms are not to be interpreted to exclude the presence of other features, steps or components.

The invention may also broadly consist in the parts, elements, steps, examples and/or features referred to or indicated in the specification individually or collectively in any and all combinations of two or more said parts, elements, steps, examples and/or features. In particular, one or more features in any of the embodiments described herein may be combined with one or more features from any other embodiment(s) described herein.

Protection may be sought for any features disclosed in any one or more published documents referenced herein in combination with the present disclosure.

Although certain example embodiments of the invention have been described, the scope of the appended claims is not intended to be limited solely to these embodiments. The claims are to be construed literally, purposively, and/or to encompass equivalents.

The invention claimed is:

1. An ostomy appliance including:

an internal collecting volume defined by a first wall and a second wall connected together about a periphery;

a stoma receiving opening defined in the first wall, a comfort layer positioned adjacent the first or second wall, an outlet portion which includes a valve having an outlet, said valve having a closed condition, in which waste is prevented or inhibited from exiting through the outlet, and an open condition, in which waste is permitted to exit through the outlet, a support panel which extends across the same first or second wall as the comfort layer and provides an opening, wherein the outlet portion has a stowed position in which the valve is housed in the opening.

2. An ostomy appliance according to claim 1 wherein the support panel extends across the second wall.

3. An ostomy appliance according to claim 1 wherein the support panel is attached at a position spaced from the periphery.

4. An ostomy appliance according to claim 3 wherein the support panel is attached across an area extending from the periphery to adjacent the opening.

5. An ostomy appliance according to claim 1 wherein the support panel is attached on both sides of the opening.

6. An ostomy appliance according to claim 5 wherein the support panel is attached along a top portion above the opening and forms a housing extending upwards from the opening.

7. An ostomy appliance according to claim 1 wherein the support panel extends around four surfaces of the outlet portion when it is in its stowed position.

8. An ostomy appliance according to claim 1 wherein the support panel includes or is attached to an extension portion.

9. An ostomy appliance according to claim 8 wherein the extension portion extends towards a bottom portion of the comfort layer.

10. An ostomy appliance according to claim 1 wherein the comfort layer is connected to the support panel.

11. An ostomy appliance according to claim 1 wherein the outlet portion includes an engagement formation for engaging a corresponding formation to hold the outlet portion in the stowed position.

12. An ostomy appliance according to claim 10 wherein the engagement formation is formed on a first wall side of the outlet portion and the corresponding formation is provided on the support panel or, optionally if additionally dependent directly or indirectly on claim 8, the corresponding formation is provided on the extension portion.

13. An ostomy appliance according to claim 11 wherein the engagement formation and the corresponding formation include respective hook-and-loop fasteners.

14. An ostomy appliance according to claim 1 wherein the support panel is more rigid than the first and/or second wall.

15. An ostomy appliance according to claim 1 wherein a lower portion of the comfort layer is not connected to the second wall.

16. An ostomy appliance according to claim 1 further including a second comfort layer adjacent the first wall and connected about the periphery.

17. An ostomy appliance according to claim 1 wherein the valve includes a closure arrangement which is moveable between a position blocking the outlet, and a second position in which the outlet is open.

18. An ostomy appliance according to claim 17 wherein the closure arrangement has a blocking member which is inserted into the outlet when the valve is in its closed condition.

19. An ostomy appliance according to claim 1 wherein the appliance is a urostomy appliance.

20. An ostomy appliance according to claim 8, wherein the comfort layer is connected to the extension portion.

* * * * *